United States Patent
Jönsson

(10) Patent No.: US 7,611,493 B2
(45) Date of Patent: Nov. 3, 2009

(54) DEVICE FOR PREVENTING AXIAL MOVEMENT

(75) Inventor: Lennart Jönsson, Furulund (SE)

(73) Assignee: Gambro Lundia AB, Lund (SE)

( * ) Notice: Subject to any disclaimer, the term of this patent is extended or adjusted under 35 U.S.C. 154(b) by 397 days.

(21) Appl. No.: 10/577,353

(22) PCT Filed: Oct. 22, 2004

(86) PCT No.: PCT/SE2004/001532

§ 371 (c)(1),
(2), (4) Date: Apr. 28, 2006

(87) PCT Pub. No.: WO2005/039683

PCT Pub. Date: May 6, 2005

(65) Prior Publication Data

US 2007/0032761 A1    Feb. 8, 2007

(30) Foreign Application Priority Data

Oct. 29, 2003    (SE) ................... 0302841

(51) Int. Cl.
*A61M 5/32* (2006.01)
(52) U.S. Cl. .................................. 604/174
(58) Field of Classification Search ............ 604/174, 604/178, 180
See application file for complete search history.

(56) References Cited

U.S. PATENT DOCUMENTS

| | | | | |
|---|---|---|---|---|
| 3,625,210 A | * | 12/1971 | Mikkelson | .......... 604/174 |
| 3,683,911 A | * | 8/1972 | McCormick | .......... 604/180 |
| 4,336,806 A | * | 6/1982 | Eldridge, Jr. | .......... 604/174 |
| 4,579,120 A | * | 4/1986 | MacGregor | .......... 600/392 |
| 4,597,632 A | * | 7/1986 | Mallinson | .......... 385/72 |
| 4,981,475 A | | 1/1991 | Haindl | |
| 5,833,666 A | | 11/1998 | Davis et al. | |
| 6,231,548 B1 | | 5/2001 | Bassett | |
| 6,258,066 B1 | * | 7/2001 | Urich | .......... 604/174 |
| 6,283,945 B1 | * | 9/2001 | Bierman | .......... 604/174 |
| 6,375,639 B1 | * | 4/2002 | Duplessie et al. | .......... 604/174 |

FOREIGN PATENT DOCUMENTS

| | | |
|---|---|---|
| GB | 2115290 | 9/1983 |
| JP | 2001-137351 | 5/2001 |
| WO | 97/21459 | 6/1997 |
| WO | 03/068304 | 8/2003 |

* cited by examiner

*Primary Examiner*—Nicholas D Lucchesi
*Assistant Examiner*—Aarti Bhatia
(74) *Attorney, Agent, or Firm*—Dilworth & Barrese LLP

(57) ABSTRACT

A device for preventing axial movement of an elongated member (1) applied through the skin of a mammal at a puncturing position has a plaster (2) designed to cover the surface around the puncturing position and having at least an adhesive layer (4) for securing it to the skin as well as an opening (9) through the layer thereof for the passage of said elongated member therethrough. The device also has a clamp (8) secured to plaster and adapted to clamp around the elongated member when the elongated member is applied to the skin and the plaster is applied on the surface around said puncturing position. The clamp is thin and substantially flat.

20 Claims, 2 Drawing Sheets

DEVICE FOR PREVENTING AXIAL MOVEMENT

BACKGROUND OF THE INVENTION AND PRIOR ART

The present invention generally relates to a device for preventing axial movement of any elongated member applied through the skin of a mammal at a puncturing position. Accordingly, the purpose of such a device is to keep said elongated member applied through the skin of a mammal for different reasons. Such an elongated member is mostly stiff and sharp, so that it may be pearced through the skin of said mammal, normally a human being, but it may also be flexible, such as a catheter, which has been pearced through the skin by using a cannula needle thereafter retracted.

More specifically, the invention relates to such a device comprising a plaster designed to cover the surface around the puncturing position and having at least an adhesive layer for securing it to the skin as well as an opening through the layer(-s) thereof for the passage of said elongated member therethrough. The plaster is used for securing the needle on the skin. By this the patient also has a visible security against the needle falling out.

A device of this type may for instance be used for preventing axial movement of a cannula needle when carrying out hemo-dialysis, in which the blood of a patient suffering from impaired kidney function is conducted from a patient blood vessel to a dialysis machine and is returned to the patient after treatment. In such a case two cannula needles may be used, one for draining blood from the patient and the other for returning the treated blood thereto. It is in this case of vital importance that a said device is extremely reliable, since it would of course be a catastrophe if the cannula needle returning the blood to the patient would move out of the correct position, so that blood would only be drained from the body of the patient without being returned. However, in this case also a single needle may be used. When a single needle is used, the blood is received from the patient and transferred back to the patient through the same needle. The needle is, in its turn, connected to a tube that is split up into two parts, one for venous blood and one for arterial blood.

Devices of this type are disclosed in for example DE 3105187, DE 19508073 and U.S. Pat. No. 5,087,248. These devices use the material of the plaster for keeping the cannula needle, catheter or the like in position. However, this material may be stretched or partially torn apart would the patient move, so that there is a risk that the elongated member moves axially. These devices also use an adhesive to keep the elongated member in place by securing wings attached to the elongated member to the skin, so that it is important that this adhesive binds strongly enough to said wings. In the case of a cannula needle, this is very thin, so it is necessary to apply an adhesive tape or the like on wings provided extra therefor at a remarkable distance from the needle portions penetrating the skin.

A device according to the preamble of appended claim 1 is known through WO 97/21459. The clamping means used for keeping the needle in place is rather complicated to the construction and is not able to hold the needle as firm as desired in some situations.

Furthermore, it may be mentioned that U.S. Pat. No. 6,231,548 and U.S. Pat. No. 5,084,026 disclose devices of another type differing from the present invention by the fact that the plaster thereof is not penetrated by the elongated member, so that the plaster does not cover the surface around the puncturing position of the elongated member. A plaster is there instead used to be carried for other means holding the elongated member in place. The devices are rather complex, secure the elongated member at a considerable distance from the puncturing position and do not use the plaster to cover the surface around the puncturing position.

SUMMARY OF THE INVENTION

The object of the present invention is to provide a device of the type defined, improving the operation reliability and accuracy with respect to such devices already known.

This object is according to the invention obtained by providing such a device with a clamping means being thin and substantially flat and provided with a lateral opening for laterally introducing a said elongated member between clamping portions thereof, and said clamping means including parts of substantially rigid material provided with clamping portions adapted to bear against a said elongated member.

It is by this construction of the clamping means possible to clamp close to the penetration point of the elongated member thereby minimizing any lever action thereon, so that the elongated member, such as a needle, may be held very firmly and reliably against axial movement thereof without the use of any adhesive strips, glue or the like. It is also comfortable to the patient if the device can be kept as this as possible.

"Clamp" should be interpreted as bearing on the elongated member under tension from at least two different directions through members, which would move closer to each other would not the elongated member be located therebetween. This is quite different than having an adhesive tape or a plaster portion secured to the elongated member therearound while only relying on the adhesive for preventing said axial movement of the elongated member.

According to an embodiment of the present invention said clamping means is of (a) material(-s) being substantially more rigid than the material(-s) forming the plaster, which facilitates the obtention of the clamping function thereof.

According to another embodiment of the invention surfaces through which the clamping portions are adapted to bear against a said elongated member are made of a substantially rigid material. This enables said clamping portions to efficiently engage circumferential surfaces of the elongated member, such as a cannula needle for firmly holding this elongated member in place through the clamping action.

According to another embodiment of the present invention said clamping means has clamping portions with sharp gripping edges adapted to bear against a said elongated member clamped thereby. This further increases the reliability of the gripping action of the clamping means.

The elongated member may for example be made of metal.

According to another embodiment of the present invention said plaster is provided with a pocket formed between two adjacent layers thereof and housing said clamping means, so that the clamping means will be an integral part of the plaster.

According to another embodiment of the present invention said clamping means is transferable between an inactive state allowing a said elongated member to be introduced between clamping portions thereof and an active state in which said clamping portions bear under tension against a said elongated member. This means that the elongated member may without any problems be introduced into the clamping means, but this may nevertheless efficiently clamp the elongated member when desired by transferring the clamping means to said active state.

According to another embodiment of the present invention constituting a further development of the embodiment last mentioned at least said clamping portions of said clamping means are made of a material having a high coefficient of thermal expansion in the region around the body temperature of a mammal for which the device is intended to be used such as to be influenced by the temperature when applied together with a plaster on the skin of a said mammal for being transferred from said inactive to said active state through the temperature rise caused through heat transfer from the body of said mammal. This way of realising the clamping means is very simple and results at the same time in a reliable function thereof. In this case at least said clamping portions of said clamping means may be made of a so-called memory metal.

According to another embodiment of the present invention said clamping means comprises at least one spring member connected to said clamping portions for urging them towards each other. One or more spring members may in this way be used for obtaining a reliable clamping action of the clamping means. "Spring member" is here to be interpreted very broadly and comprises all types of members acting as a spring by trying to lower the potential energy thereof by changing shape.

According to another embodiment of the present invention associated with the embodiment last mentioned the device comprises a blocking member adapted to hold the clamping portions apart in said inactive state for allowing introduction of a said elongated member therebetween and when released allowing said spring member to transfer the clamping means to the active state, so that such a spring member may be used to efficiently clamp an elongated member without making it difficult to introduce the elongated member into the clamping means.

According to another embodiment of the present invention the device comprises an elongated flexible, preferably adjustable, such as by being elastic, band-like member secured to the plaster and adapted to be applied around a body part of a mammal on which a said puncturing position has been applied for assisting the adhesive layer of the plaster in holding the plaster secured around the puncturing position, so that the holding of the plaster and by that the clamping means in place is further improved.

Further features of the present invention appear from the following description.

BRIEF DESCRIPTION OF THE DRAWINGS

With reference to the appended drawings, below follows a specific description of various embodiments of the present invention cited as examples.

In the drawings.

DESCRIPTION OF THE PREFERRED EMBODIMENTS

Figure 1:
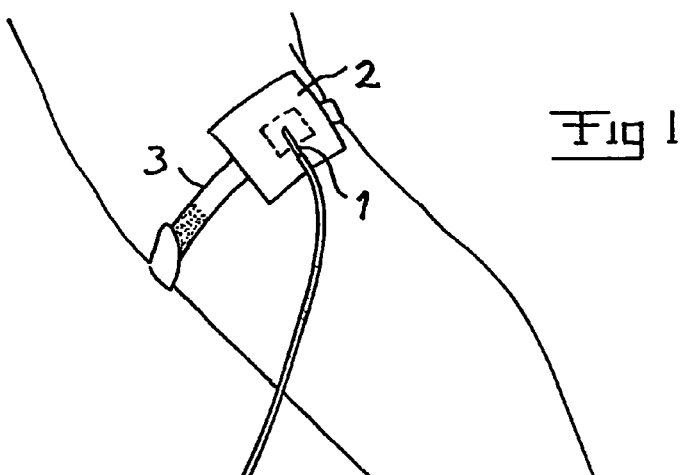
FIG. 1 is a schematic perspective view illustrating a typical use of a device according to the present invention.

FIG. 1 schematically illustrates the use of a device according to the present invention for preventing axial movement of en elongated member in the form of a cannula needle 1 applied through the skin of an arm of a human for draining blood from a vein or supplying a fluid, preferably blood, but possibly also for instance anaesthetic thereinto. It is stressed that the most critical thing is to return blood to the patient. The cannula needle is passing through a plaster 2 being secured to the skin by an adhesive layer thereon and further secured to the arm of a patient by a band 3 secured to the plaster and applied around the arm while forming a loop through using for instance a hook- and loop-fastener. The band 3 is preferably adjustable, possibly by being elastic for adapting it to the body of the patient and efficiently assisting the adhesive layer of the plaster in holding the plaster in place without causing inconveniences to the patient. The cannula needle 1 is in fact firstly put in place and thereafter the plaster 2 is arranged over the puncturing position.

Figure 2:
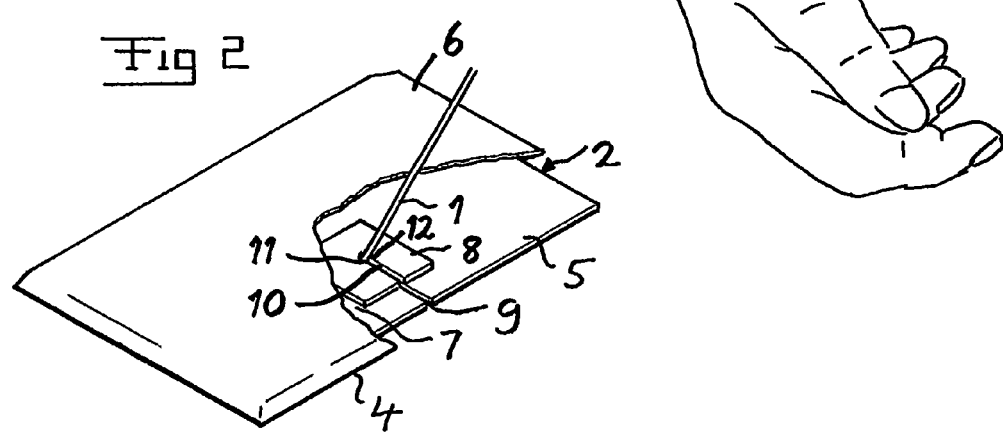
FIG. 2 is a partially sectioned perspective view illustrating the general construction of a device according to the present invention, FIG. 3 schematically illustrated a clamping means according to an embodiment of the present invention, FIG. 4 schematically illustrates a clamping means according to another embodiment of the present invention, and FIGS. 5-7 schematically illustrate clamping means including at least one spring member according to other embodiments of the present invention.

FIG. 2 illustrates the principal construction of a device according to the present invention. The plaster 2 has an adhesive layer 4 for securing it to the skin, a carrier layer 5 on top thereon and an uppermost force absorbing coating layer 6, preferably made of conventional plaster fabric material. A pocket 7 is formed between the carrier layer and the coating layer 6 for housing a clamping means 8 made of a material being substantially more rigid than the material forming the plaster. The material of the clamping means may for instance be metal or hard plastic. Different parts of the clamping means may also be made of different materials.

The plaster has a lateral slot 9 and the clamping means has a lateral slot 10 for introducing an elongated member into the opening of the plaster and between clamping portions 11, 12 of the clamping means, respectively. Accordingly, the elongated member is firstly applied through the skin at a puncturing position, so that this puncturing position is perfectly visible when applying the elongated member, such as a cannula needle. The plaster is then moved laterally with respect to the elongated member so that this is introduced into the slots 9 and 10 to the position shown in FIG. 2, whereupon the adhesive layer of the plaster is pressed against the surface of the skin surrounding the puncturing position. If the elongated member is not applied perpendicularly to the skin surface the plaster is applied with the slots 9, 10 so that the inclined elongated member when seen in a direction perpendicular to the plaster surface will extend in the direction of the slots. This means that the clamping portions forming opposite surfaces of the slot 10 of the clamping means will not try to pivot the elongated member when clamping it. Thus, the elongated member is clamped through parts of rigid material provided with clamping portions 11, 12 adapted to bear against the elongated member and acting thereupon substantially in a plane in parallel with the surface of the skin upon which the plaster is arranged. Furthermore, the elongated member is intended to extend through the clamping means between the clamping portions thereof while making a large angle with the plaster, preferably extending substantially perpendicularly thereto.

Figure 3:
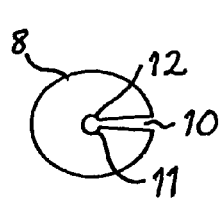
Figure 4:
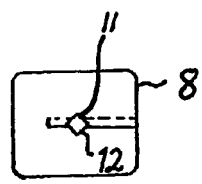

FIG. 3 and. FIG. 4 illustrate two possible constructions of the clamping means. These are thin and disc-like members made of a memory metal having a high coefficient of thermal expansion in the region around the body temperature of a mammal, mostly a human, for which the device is intended to be used such as to be influenced by the temperature when applied together with the plaster on the skin of a said mammal for being transferred from an inactive state shown for the embodiment in FIG. 3 allowing the introduction of an elongated member between the clamping portions 11, 12 or claws thereof to an active state, in which the clamping portions clamp around an elongated member, as shown for the embodiment according to FIG. 4, through the temperature rise caused through heat transfer from the body of the human.

Figure 5:
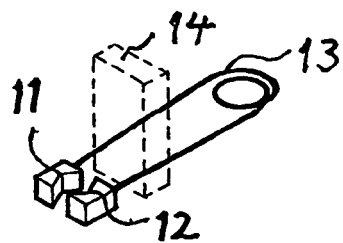

FIG. 5 illustrates how the clamping means may comprise a spring member 13 connected to the clamping portions 11, 12 for urging them towards each other. It is also schematically illustrated through dashed lines how the device may comprise a blocking member 14 adapted to hold the clamping portions apart in an inactive state of the clamping means for allowing introduction of an elongated member therebetween and when released, here displaced, allowing the spring member 13 to transfer the clamping means to the active state while urging the clamping portions 11, 12 towards each other. This blocking member has preferably a reversable function, e.g. it is then possible to re-enter the blocking member in order to be able to release the needle from its clamp position.

Figure 6:
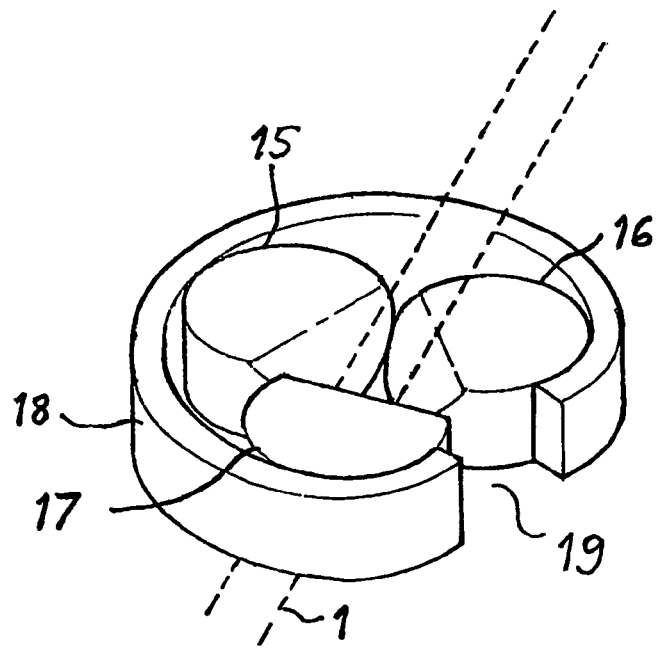

FIG. 6 illustrates a clamping means having three rings 15-17 with outer sharp edges pressed against each other through a spring band 18 having an opening 19, through which an elongated member may be introduced laterally between the rings while pressing them apart. Once the elongated member is introduced between the rings the spring band 18 will urge the clamping portions formed by the outer ring surfaces with the edges towards each other for firmly clamping the elongated member.

Figure 7:
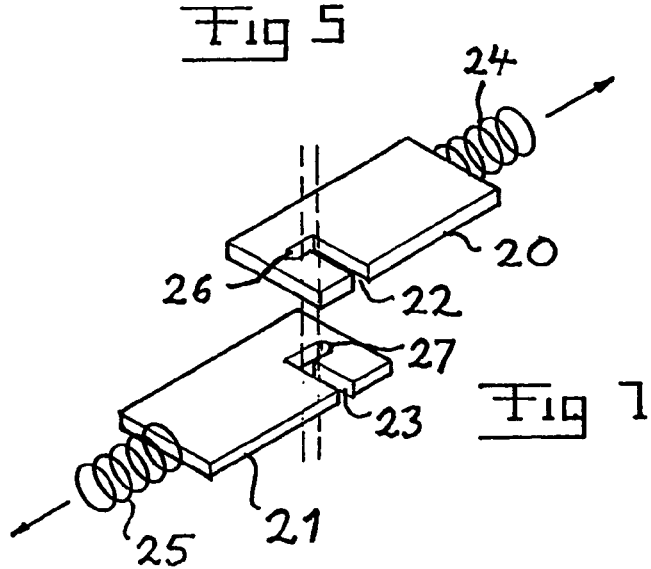

FIG. 7 illustrates a further possible embodiment of a clamping means to be secured to a plaster in a device according to the present invention. This clamping means has two plates 20, 21 with lateral slots 22, 23 for being laterally moved into engagement with an elongated member. Spring members 24, 25 are associated with the respective plate for trying to move them apart while clamping an elongated member introduced into the slots 22, 23 through bottom surfaces 26, 27 thereof. In this case a blocking member in the form of for instance a thread (not shown) to be cut off for the transfer from the inactive to the active state of the clamping means may be applied. This embodiment may be slightly modified for using compressive forces instead of tension forces. The bottom surfaces would then be oppositely directed and the spring members 24, 25 replaced by compressive springs or other compressive means pressing the plates towards each other.

The invention is of course not in any way restricted to the embodiments disclosed but may be varied and modified within the scope of the appended claims.

The elongated member may be provided with intended irregularities over a portion thereof for improving the grip of the clamping means on the elongated member.

The invention claimed is:

1. A device for preventing axial movement of an elongated member (1), such as a cannula needle, applied through the skin of a mammal at a puncturing position, said device comprising
a plaster (2) structured and arranged to cover a surface around the puncturing position and having at least an adhesive layer (4) for securing to the skin and an opening (9) through the layer (4) thereof for the passage of said elongated member (1) therethrough,
the device further comprising
means (8) secured to the plaster (2) and structured and arranged to clamp around said elongated member (1) when the elongated member (1) is applied through the skin of a mammal and the plaster (2) is applied on the surface around said puncturing position, wherein
said clamping means (8) is thin and substantially flat and provided with a lateral opening (10) for laterally introducing said elongated member (1) between clamping portions (11, 12) thereof, and said clamping means (8) includes parts of substantially rigid material provided with said clamping portions (11, 12) which are structured and arranged to bias from at least two different directions against said elongated member (1).

2. A device according to claim 1, wherein said clamping means (8) is made of material being substantially more rigid than the material forming the plaster (2).

3. A device according to claim 1, wherein surfaces through which the clamping portions (11, 12) are structured and arranged to bear against a said elongated member are made of a substantially rigid material.

4. A device according to claim 1, wherein said clamping means (8) has clamping portions (11, 12) with sharp gripping edges structured and arranged to bear against a said elongated member clamped thereby.

5. A device according to claim 1, wherein said clamping means (8) is made of metal.

6. A device according to claim 1, wherein said plaster (2) is provided with a pocket (7) formed between two adjacent layers (5, 6) thereof and housing said clamping means (8).

7. A device according to claim 6, wherein said plaster (2) comprises at least two additional layers (5, 6) besides said adhesive layer (4), and said pocket (7) is formed between two such additional layers (5, 6).

8. A device according to claim 7, wherein the plaster (2) comprises a carrier layer (5) arranged on top of the adhesive layer (4) and an uppermost coating layer (6), and said pocket (7) is formed between said carrier layer and coating layer (6).

9. A device according to claim 1, wherein said clamping means (8) is transferrable between an inactive state allowing said elongated member (1) to be introduced between clamping portions (11, 12) thereof and an active state in which said clamping portions (11, 12) bias against said elongated member (1).

10. A device according to claim 9, wherein at least said clamping portions (11, 12) of said clamping means are made of a material having a high coefficient of thermal expansion in the region around body temperature of the mammal for which the device is used and structured and arranged to be influenced by the temperature when applied together with the plaster (2) on skin of said mammal for being transferred from said inactive to said active state through the temperature rise caused through heat transfer from the body of said mammal.

11. A device according to claim 10, wherein at least said clamping portions (11, 12) of said clamping means are made of a memory metal.

12. A device according to claim 9, wherein said clamping means (8) comprises at least one spring member (13, 18, 24, 25) connected to said clamping portions (11, 12) for urging them towards each other.

13. A device according to claim 12, additionally comprising a blocking member (14) strucuted and arranged to hold the clamping portions (11, 12) apart in said inactive state for allowing introduction of said elongated member (1) therebetween and, when released, allowing said spring member (13, 18, 24, 25) to bias the clamping means (8) to the active state.

14. A device according to claim 1, wherein said plaster opening (9) is formed by a lateral slot into the plaster (2) for enabling introduction of said elongated member (1) into said opening (9) after the elongated member (1) has been applied through the skin of the mammal.

15. A device according to claim 1, additionally comprising an elongated flexible, preferably adjustable, such as by being elastic, band-like member (3) secured to the plaster (2) and structure and arranged to be applied around a body part of the mammal on which said puncturing position has been applied for assisting the adhesive layer (4) of the plaster (2) in holding the plaster (2) secured around the puncturing position.

16. A device for preventing axial movement of an elongated member (1), such as a cannula needle, applied through the skin of a mammal at a puncturing position, said device comprising
- a plaster (2) structured and arranged to cover a surface around the puncturing position and having at least an adhesive layer (4) for securing to the skin and an opening (9) through the layer (4) thereof for the passage of said elongated member (1) therethrough,
- the device further comprising
- means (8) secured to the plaster (2) and structured and arranged to clamp around said elongated member (1) when the elongated member (1) is applied through the skin of a mammal and the plaster (2) is applied on the surface around said puncturing position,
- said clamping means (8) is thin and substantially flat and includes parts of substantially rigid material provided with clamping portions (11, 12) structured and arranged to bear against said elongated member (1), wherein
- said clamping means (8) and plaster (2) are provided with a lateral slot-formed opening (9,10) structured and arranged for laterally introducing said elongated member (1) between clamping portions (11, 12) of said clamping means (8) by moving the plaster (2) with said clamping means (8) laterally with respect to said elongated member (1) applied through the skin, and
- said clamping portions (11, 12) are structured and arranged to bear against said elongated member (1) while acting thereupon substantially in a plane in parallel with the surface of the skin upon which the plaster (2) is arranged.

17. A device according to claim 16, wherein said clamping means (8) is structured and arranged to clamp said elongated member (1) extending through said clamping means (8) between said clamping portions (11, 12) at a large angle with respect to said plaster (2).

18. A device according to claim 17, wherein said large angle is about 90°.

19. A device according to claim 16, wherein said clamping portions (11, 12) are structured and arranged to bias from at least two different directions against said elongated member (1).

20. A device according to claim 16, wherein said clamping means (8) is transferrable between an inactive state allowing said elongated member (1) to be introduced between clamping portions (11, 12) thereof and an active state in which said clamping portions (11, 12) bias against said elongated member (1).

* * * * *